United States Patent
Kaar et al.

(10) Patent No.: US 9,901,597 B2
(45) Date of Patent: Feb. 27, 2018

(54) METHOD FOR INACTIVATION/REMOVAL OF COAGULATION FACTORS BY PRECIPITATION

(75) Inventors: Waltraud Kaar, Vienna (AT); Alfred Zochling, Vienna (AT); Karin Ahrer, Vienna (AT)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 13/980,894

(22) PCT Filed: Feb. 3, 2012

(86) PCT No.: PCT/EP2012/051873
§ 371 (c)(1),
(2), (4) Date: Sep. 26, 2013

(87) PCT Pub. No.: WO2012/104418
PCT Pub. Date: Aug. 9, 2012

(65) Prior Publication Data
US 2014/0007547 A1 Jan. 9, 2014

Related U.S. Application Data

(60) Provisional application No. 61/457,226, filed on Feb. 4, 2011, provisional application No. 61/509,220, filed on Jul. 19, 2011.

(30) Foreign Application Priority Data

Feb. 4, 2011 (EP) ..................... 11153349
Jul. 19, 2011 (EP) ..................... 11174559

(51) Int. Cl.
| | | |
|---|---|---|
| A61K 35/14 | (2015.01) |
| A61K 35/16 | (2015.01) |
| C07K 16/00 | (2006.01) |
| C07K 14/76 | (2006.01) |

(52) U.S. Cl.
CPC ............ *A61K 35/14* (2013.01); *A61K 35/16* (2013.01); *C07K 14/76* (2013.01); *C07K 16/00* (2013.01)

(58) Field of Classification Search
CPC ........ C07K 14/76; C07K 16/00; A61K 35/14; A61K 35/16
See application file for complete search history.

(56) References Cited

FOREIGN PATENT DOCUMENTS

| EP | 0 987 274 A1 | 3/2000 |
|---|---|---|
| EP | 1 816 201 A1 | 8/2007 |
| GB | 906 860 A | 9/1962 |
| WO | WO 2005/082937 A2 | 9/2005 |
| WO | WO2005082937 † | 9/2005 |
| WO | WO 2007/085626 A1 | 8/2007 |
| WO | WO2007085626 † | 8/2007 |

OTHER PUBLICATIONS

Lebing et al. Properties of a new intravenous immunoglobulin (IGIV-C, 10%) produced by virus inactivation with caprylate and column chromatography. Vox Sanguinis, 84, Jan. 7, 2003, pp. 193-201.
Radosevich et al. Intravenous immunoglobulin G: trends in production methods, quality control and quality assurance, VOX Sanguinis, 98, Jun. 29, 2009, pp. 12-28.
Steinbuch et al. Isolement de L'Immunoglobuline IgG Du Plasma Humain a L'Aide de L'Aciden Caprylique, Rev. Franc. Etudes Clin. Et Biol., 1969 XIV, 1054-1058.
Williams et al. J. Allergy Clin Innumol., Abstract 34, Removal of Coagulation Factros by the Gamunex-C Purification Process, AAAA1 Annual Meeting (Feb. 22-26, 2013).
Anonymous, "Allgemeine Hinweise", May 1, 2010, XP002681510, Retrieved from the Internet: URL:http//www.ganzimmun.de/item_doc/v/allgemeine_hinweise.pdf.
Anonymous, "Allgemeine Hinweise", May 1, 2010, XP002681510, p. 5, Paragraphs 1-2, retrieved from the Internet: http://ganzimmun.de/item_doc/lv/allgemeine_hinweise.pdf, Germany.
Bonna N. Bouma and John H. Griffin, "Human Blood Coagulation Factor XI—Purification, Properties, and Mechanism of Activiation by Activated Factor XII", The Journal of Biological Chemistry, vol. 252, No. 18, Issue of Sep. 25, 1977, pp. 6432-6437, United States of America.
Yutaka Komiyama, Takashi Murakami, Hiroshi Egawa, Susumu Okubo, Kojiro Yasunaga and Kenjiro Murata, "Purification of Factor XIa Inhibitor from Human Platelets", Thrombosis Research 66, pp. 397-408, 397-408, 0049-3838/92, Copyright 1992, Pergamon Press, Ltd., United States of America.
Radosevich et al. Intravenous Immunoglobulin G: Trends in Production Methods, Quality Assurance. Vox Sanguinis, (2010), 98, 12-28.
Steinbuch and Audran, English Abstract of "Isolement de l'immunoglobuline IgG du plasma humain a l'aide de l'acide caprylique," Rev. Franc. Etudes Clin. et Biol., vol. XIV, pp. 1054 and 1057, 1969.†
Williams et al., "Removal of coagulation factors by the Gamunex-C purification process," J. Allergy Clin. Immunol., Abstract 34, Feb. 22-26, 2013, AAAAI Annual Meeting, San Antonio, TX.†
Lebing et al., "Properties of a new intravenous immunoglobulin (IGIV-C, 10%) produced by virus inactivation with caprylate and column chromatography," vol. 84, pp. 193-201, 2003.†

† cited by third party

*Primary Examiner* — John Kim
(74) *Attorney, Agent, or Firm* — Jacobson Holman PLLC

(57) ABSTRACT

A method for inactivation or removal of coagulation factors FII, FVII, FVIIa, FIX, FIXa, FX, FXI and FXIa in or from protein containing solutions obtained from blood, blood plasma, plasma fractions or by recombinant means wherein the protein containing solution is contacted with an organic acid or its salt while being stirred.

12 Claims, No Drawings

METHOD FOR INACTIVATION/REMOVAL OF COAGULATION FACTORS BY PRECIPITATION

This is a 371 of PCT/EP12/051873 filed Feb. 3, 2012, which has a priority of European no. 11153349.3 filed Feb. 4, 2011, US provisional application No. 61/457,226, filed Feb. 4, 2011, European no. 11174559.2 filed Jul. 19, 2011, and U.S. provisional application No. 61/509,220, filed Jul. 19, 2011, hereby incorporated by reference.

This invention provides a method for inactivation of coagulation factors present in protein preparations derived from blood, blood plasma or by recombinant methods.

INTRODUCTION

As part of the contact activation or intrinsic pathway of the coagulation cascade coagulation factors play a major role in blood coagulation and clot formation. As evidences exist that some coagulation factors, e.g. FXI, may be activated during manufacturing of pharmaceuticals it appears a necessity to eliminate or at least inactivate such activated coagulation factors. It is even more preferable to remove as many coagulation factors as possible from therapeutic preparations intended for intravenous or subcutaneous application in order to omit unwanted and health endangering clot formation in form of thrombotic events in patients.

Methods for reduction of FXIa or FXI occurring in solution admixed with other proteins, such as immunoglobulins or albumin, are known but include time consuming methods based on chromatography which also represent substantial investments when specific affinity resins are used.

Bouma et al.; J. Biol. Chem.; 1977; 252(18); 6432-7 teaches purification of FXI containing no measurable amount of FXIa (less than 0.01 U/ml) from blood plasma by four successive chromatographic steps starting with DEAE-chromatography followed by QAE- and SP-chromatography and a second chromatographic step with SP-Sephadex. In some occasions an additional chromatographic purification on concanavalin A-Sepharose affinity gel was performed to eliminate gamma-globulin (immunoglobulin G).

Komiyama et al; Thromb. Res.; 1992; 66; 397-408 describes a method for removal of FXI/FXIa from platelet concentrates with the help of immobilized antibodies directed against FXI.

SUMMARY OF THE INVENTION

Subject-matter of the present invention is to provide a method for inactivation and/or removal of activated coagulation factors and their not activated zymogens from sources containing such proteins. The present invention discloses a method for inactivation and/or removal of activated and/or non-activated coagulation factors, in particular coagulation factors FXIa and FXI but also, FII, FVII, FVIIa, FIX, FIXa, and FX in or from a source containing such coagulation factors. Sources of interest are blood or blood plasma or fractions thereof, in particular fractions of blood plasma containing as therapeutically active proteins predominantly immunoglobulins or albumin.

It was surprisingly found that contacting a coagulation factor containing immunoglobulin G (IgG) solution with an organic acid or its salt while being stirred at a temperature from about 0° C. to about 40° C., in the pH range from about 3.5 to about 6.0, not only inactivated or removed FXIa but also other coagulation factors. The organic acid may be a $C_4$ to $C_{10}$, saturated or unsaturated organic acid or its salts, in particular salts of alkaline earth metals such as sodium salts.

In one embodiment of the invention the organic acid is butyric (C4), valeric (C5), caproic (C6), enanthic (C7), caprylic (C8), pelargonic (C9), and/or capric (C10) acid or its salts such as sodium salts. In particular, the organic acid is caprylic acid or its salt is sodium caprylate but also the salts of valeric acid and capric acid were found to be well suited.

Applied concentrations of the organic acid or its salt were within the range of from 5 to 50 mmol/l. Proteins and the organic acid or its salt were stirred for a time of from 45 to 180 minutes, in particular from 55 to 120 minutes and the developing precipitate was separated from the supernatant. Filtration aids such as silicates, e.g. naturally occurring or synthesized silicates selected from diatomaceous earth, fumed silica, perlites or zeolithes, may optionally be present while stirring. This inactivation or removal step is advantageous since it may be introduced in any known process for purification of blood derived proteins wherever it appears appropriate. Resulting protein solutions were further handled as known from prior art. The method is in particular suitable for manufacturing immunoglobulin G preparations.

DETAILED DESCRIPTION OF THE INVENTION

The present invention provides a method for inactivation and/or removal of coagulation factors from sources containing such proteins. Examples for such sources represent protein solutions containing predominantly immunoglobulins, in particular immunoglobulin G (IgG) or albumin. Chromatographic manipulations for removal of coagulation factors FII, FVII, FVIIa, FIX, FIXa, FX, FXI and FXIa can be avoided by the present invention. Of course, chromatographic purification steps may be employed additionally for other reasons.

Surprisingly it was found that contacting a solution containing a complex mixture of coagulation factors, in particular Fraction I+II+III from plasma fractionation or comparable fractions, with an organic acid or its salt, in particular the sodium salt, at a temperature from about 1° C. to about 40° C., in particular from 2° C. to 30° C., and a broad pH range from about 4.0 to about 6.0, in particular from 4.2 to 5.6 inactivated or removed said coagulation factors to be beyond the detection limit. It was additionally observed that factor XI-antigen (FXI:Ag) values were reduced to below 5 mIU/mg IgG, when the solution was contacted with caprylic acid or its salt at a concentration of at least 20 mmol/l. The pH value may shift within said range or may be kept essentially constant within this range with a deviation of +/−0.3 from a fixed value during the treatment with the organic acid or its salt. Applied concentrations of the organic acid or its salt, in particular sodium caprylate are within the range of from 5 to 50 mmol/l, in particular from 10 to 22 mmol/l. Proteins and the organic acid or its salt are allowed to be contacted under constant stirring from 45 to 180 minutes, in particular from 55 to 120 minutes. A filtration aid such as silicates, e.g. naturally occurring or synthesized silicates selected from diatomaceous earth, fumed silica, perlites or zeolithes, may optionally be present during the stirring; and is removed together with developing precipitate after the contacting. Separation of precipitate and supernatant may be performed by methods generally known and can be performed by filtration, centrifugation or settlement and requires in general another 60 to 120 minutes. Separation by settlement may take longer. One cycle of precipitation and separation may accordingly last up to 5 hours from starting the precipitation until the end of separation. In particular, if the first inactivation or removal may be insufficient to completely inactivate or remove some of the coagulation factors as residual amounts of these factors above the detection limit may occur, it may be advisable to perform a second inactivation or removal step. Methods for separation of precipitate and supernatant are well known and incorporate sedimentation, filtration or centrifugation or a combination thereof. A second inactivation by the organic acid or its salt may thus be incorporated as an option. This inactivation or removal step may be introduced in any known process for purification of blood derived proteins wherever it appears appropriate. Resulting protein solutions are further handled as known from prior art. Conventional treatment includes anion chromatography for removal of residual amounts of organic acid or its salt, solvent/detergent treatment (S/D treatment), ultra- and diafiltration, formulation, sterile filtration and filling into final containers. The product may as an option also be subjected to lyophilisation. The concentration of the final IgG product is usually in the range of 5-16% IgG but also concentrations up to about 25% are possible. It has to be mentioned that concentrations higher than 20% require specific formulation due to viscosity reasons when applied intravenously. IgG recovery was found to benefit from treatment of one organic acid or its salt at low temperatures from about 2-8° C. followed after separation of precipitate by a treatment with a different organic acid or its salt at room temperatures of 20-40° C. One example of such a process is the treatment with sodium caprylate at 2-8° C. combined with treating the solution after separation of precipitate with sodium valerate or sodium caprate at 20-40° C.

Analytical Methods

To ensure that no activation or concentration of coagulation factors took place during the manufacturing process, in-process samples were drawn over the whole process and analyzed on the coagulation factors described above. All in-process samples as well as product in final containers were tested for occurrence of coagulation factors. At the latest from the second treatment with organic acid or its salt on detection of coagulation factors was not possible due to removal or inactivation. The detection limit of coagulation factors was even in concentrated final products not reached or exceeded. In addition, the procoagulant activity of the final products were analyzed with NATEM and thrombin generation assay (TGA). For all final products no clotting activity was detected.

Procoagulant Activity

Procoagulant activity was measured on the ROTEG® Coagulation Analyzer available from PENTAPHARM® based on the principles of thrombelastography with the NATEM® test and Star-tem® reagents available from ROTEM® in factor XI deficient plasma. All assays were conducted with final product (IgG concentrations 5%, 10% and 16%) and aborted after more than 3000 seconds (50 minutes) revealing no procoagulant activity.

Thrombin Generation Assay

The thrombin generation assays (TGA) were performed on the TECHNOTHROMBIN® TGA of Technoclone in factor XI deficient plasma and as well as in pooled normal plasma. Lag-time, i.e. the onset of thrombin formation, peak thrombin and TTP, i.e. time-to-peak, were determined. The results were summarized in Table 1 revealing somewhat prolonged lag-times and TTP in Factor XI deficient plasma (FXI-PD) and a reduction in peak thrombin to about 10% of plasma pool values.

TABLE 1

| | TGA plasma pool | | | TGA FXI-DP | | |
|---|---|---|---|---|---|---|
| n = 26 | lag time [min] | peak thrombin [nM] | TTP [min] | lag time [min] | peak thrombin [nM] | TTP [min] |
| mean | 14.9 | 254.9 | 23.2 | 17.5 | 25.2 | 32.2 |
| range | 11.1-19.1 | 204-363 | 19.1-29.1 | 16.6-27.6 | 21-31 | 31.6-45.1 |

Analyses of Factors FII, FVII, FVIIa, FIX, FIXa, FX, FXI and FXIa

Clotting activities of said factors were determined on an ACL 10000 coagulation analyzer of Werfen Group with relevant test kits with the exemption of FIXa and FXIa, which were analysed with the BIOPHEN® Factor IXa testkit (HYPHEN® BioMed) and a modification thereof. Clotting activity of FXIa was measured based on the BIOPHEN® Factor IXa testkit, addition of recombinant FIX and calibration with a FXIa concentrate. While an initial calibration curve for FIXa just allowed analyses to a lower detection limit of 1.0 mIU/ml, a second calibration curve ("low calibration concentration curve") allowed analyses to a lower detection limit of 0.32 mIU/ml. Consequently, both limits can be found in the tables of analytical results. Results were summarized in tables below. Values given as "<" indicate that the detection limit was not reached, some mean values in table 2 indicate a value lower than the detection limit which indicates that not all values were under the detection limit, these mean values were calculated as the sum of half of the detection limit for results "<" and the actual value found for those results above the detection limit. Alternatively to said calculated values with the half of the detection limit, a calculation with the value of the detection limit was performed as worst case scenario revealing 0.015 IU/ml FVII, 8.4 mIU/ml FVIIa, 0.016 IU/ml FIX, 1.12 mIU/ml FIXa and 1.0 mIU/ml FXIa.

In case that any residual amounts of FII should exist at concentrations lower than the detection limit of 0.014 IU/ml it is to be understood that this amount is within the range of 0.001 to 0.014 IU/ml FII. The same is true for FVII with a detection limit of 0.015 IU/ml and a range of 0.001 to 0.015 IU/ml, for FVIIa with a detection limit of 8.4 mIU/ml and a range of 0.1 to 8.4 mIU/ml, for FIX with a detection limit of 0.016 IU/ml and a range of 0.001 to 0.016 IU/ml, for FIXa with a detection limit of 1.12 mIU/ml and a range of 0.01 to 1.12 mIU/ml, for FX with a detection limit of 0.015 IU/ml and a range of 0.001 to 0.015 IU/ml, for FXI with a detection limit of 0.014 IU/ml and a range of 0.001 to 0.014 IU/ml. And also for FXIa, determined with the low concentration calibration curve, with a detection limit of 0.32 mIU/ml and a range of 0.01 to 0.32 mIU/ml, while the initially used calibration curve just allowed a detection limit of 1.0 mIU/ml, consequently, the range is therefore 0.01 to 1.00 mIU/ml.

EXAMPLES

Example 1 (Sodium Caprylate)

Fraction I+II+III from plasma fractionation was dissolved and cooled to 2-8° C. and the pH was kept constant in the range of 4.80-4.95 when sample A was drawn from this solution. Sodium caprylate was added to a final concentration of 20 mmol/l and the solution was stirred for 90 minutes before filtration. After drawing sample B the filtered solution was heated to 21-27° C., the pH was still kept constant at about 4.9 in the given range and caprylate was again added to a concentration of 20 mmol/l. After stirring for 60 minutes and centrifugation sample C was drawn from the supernatant and all samples were assayed. The supernatant was further processed by anion chromatography, virus inactivation (S/D treatment), ultra- and diafiltration, formulation, sterile filtration and filling to the final product.

Example 2

Essentially the same procedure as example 1 was performed with the exemption that an amount of 10 mmol caprylate was added per liter solution for the second precipitation instead of adjustment to 20 mmol/l.

Examples 3 and 4

The same procedure as example 2 was performed with the sodium salts of valeric acid and capric acid.

TABLE 2

Process according to examples 1 and 2 as no significant differences in clotting activities were observed: Although later experiments (see tables 4 to 7) revealed significantly higher amounts of of coagulation factors in the source material prior to addition of the precipitant the inventive method presented herein managed to eliminate these factors. Even in concentrates of 10% IgG there were no coagulation factors measureable.

| Coagulation factors | Sample A (resusp. fraction I + II + III) | | Sample B (after $1^{st}$ precipitation) | | Sample C (after $2^{nd}$ precipitation) | |
|---|---|---|---|---|---|---|
| | Mean | Range | Mean | Range | Mean | Range |
| FII [IU/ml] | 0.30 | 0.21-0.56 | <0.014 | <0.014 | <0.014 | <0.014 |
| FVII [IU/ml] | 5.48 | 3.9-9.5 | 0.012 | <0.015-0.019 | <0.015 | <0.015 |
| FVIIa [mIU/ml] | 1477.3 | 1066-2108 | 5.4 | <8.4-10.2 | <8.4 | <8.4 |
| FIX [IU/ml] | 3.10 | 3.10 | 0.010 | <0.016-0.019 | <0.016 | <0.016 |
| FIXa [mIU/ml] | 115.5 | 55.9-231.0 | 0.70 | <1.12-1.24 | <1.12 | <1.12 |
| FX [IU/ml] | 0.05 | 0.02-0.12 | <0.015 | <0.015 | <0.015 | <0.015 |
| FXI [IU/ml] | 1.31 | 0.93-1.81 | <0.014 | <0.014 | <0.014 | <0.014 |
| FXIa [mU/ml] | 113.9 | 10.9-339.2 | 1.9 | <1.0-3.9 | <1.0 | <1.0 |

| Coagulation factors | Sample D (concentrated to 7% IgG) | | Sample E (final container - 10% IgG) | |
|---|---|---|---|---|
| | Mean | Range | Mean | Range |
| FII [IU/ml] | <0.014 | <0.014 | <0.014 | <0.014 |
| FVII [IU/ml] | <0.015 | <0.015 | <0.015 | <0.015 |
| FVIIa [mIU/ml] | <8.4 | <8.4 | <8.4 | <8.4 |
| FIX [IU/ml] | <0.016 | <0.016 | <0.016 | <0.016 |
| FIXa [mIU/ml] | <1.12 | <1.12 | <1.12 | <1.12 |
| FX [IU/ml] | <0.015 | <0.015 | <0.015 | <0.015 |
| FXI [IU/ml] | <0.014 | <0.014 | <0.014 | <0.014 |
| FXIa [mU/ml] | <1.0 | <1.0 | <1.0 | <1.0 |

TABLE 3

Process according to examples 3 and 4:

| Coagulation factors | Sample A (resusp. fraction I + II + III) | | Sample B (after $1^{st}$ precipitation) | | Sample C (after $2^{nd}$ precipitation) | |
|---|---|---|---|---|---|---|
| | Capric acid salt | Valeric acid salt | Capric acid salt | Valeric acid salt | Capric acid salt | Valeric acid salt |
| FII [IU/ml] | na | na | na | na | na | na |
| FVII [IU/ml] | 15.5 | 15.3 | 1.50 | 0.19 | <0.015 | <0.015 |
| FVIIa [mIU/ml] | 3945.0 | 3547.0 | 1026.00 | 142.00 | <8.4 | 9.1 |
| FIX [IU/ml] | 8.30 | 7.50 | 0.36 | 0.07 | <0.016 | <0.016 |
| FIXa [mIU/ml] | 368.0 | 358.0 | 68.00 | 6.40 | <1.12 | <1.12 |
| FX [IU/ml] | 0.22 | 0.34 | <0.015 | <0.015 | <0.015 | <0.015 |
| FXI [IU/ml] | na | na | 0.32 | 0.033 | <0.014 | <0.014 |
| FXIa [mU/ml] | 102.0 | 114.0 | 20.6 | 14.7 | <1.0 | <1.0 |

TABLE 4

| | | Precipitations with pH value kept constant | | | | | | | | |
|---|---|---|---|---|---|---|---|---|---|---|
| Organic acid/salt | | caprylic | caprylic | | caprylic | caprylic | | caprylic | caprylic | |
| Organic acid/salt | [mM] | 20 | 10 | | 20 | 10 | | 20 | 20 | |
| pH value | | 4.7 | 4.7 | | 5.1 | 5.1 | | 4.5 | 4.5 | |
| Temperatur | [° C.] | 2 | 21 | | 2 | 27 | | 5 | 25 | |
| Stirring | [min] | 55 | 55 | | 90 | 90 | | 70 | 70 | |
| Sample | | A | B | C | A | B | C | A | B | C |
| FII | [IU/ml] | 0.82 | 0.017 | <0.014 | 1.15 | <0.014 | <0.014 | 0.64 | 0.02 | 0.014 |
| FVII | [IU/ml] | 5.04 | 0.023 | <0.015 | 5.05 | <0.015 | <0.015 | 4.99 | 0.05 | <0.015 |
| FVIIa | [mIU/ml] | 4090 | 31 | <8.4 | 4375 | 5.5 | <8.4 | 3604 | 59 | <8.4 |
| FIX | [IU/ml] | 4.12 | 0.09 | <0.016 | 5.20 | <0.016 | <0.016 | 2.47 | 0.059 | <0.016 |
| FIXa | [mIU/ml] | 293.8 | 14.2 | <1.12 | 296.7 | <1.12 | <1.12 | 280.5 | 15 | <1.12 |
| FX | [IU/ml] | 0.27 | <0.015 | <0.015 | 0.18 | <0.015 | <0.015 | 0.34 | 0.02 | <0.015 |
| FXI | [IU/ml] | 3.56 | 0.11 | <0.014 | 4.24 | <0.014 | <0.014 | 3.43 | 0.17 | <0.014 |
| FXIa | [mU/ml] | 551 | 36.7 | <0.32 | 176 | 1.20 | <0.32 | 226 | 33 | <1.0 |
| Organic acid/salt | | caprylic | caprylic | | caprylic | caprylic | | caprylic | caprylic | |
| Organic acid/salt | [mM] | 20 | 10 | | 20 | 10 | | 20 | 10 | |
| pH value | | 5.1 | 5.1 | | 5.1 | 5.1 | | 5.1 | 5.1 | |
| Temperatur | [° C.] | 8 | 27 | | 8 | 27 | | 2 | 21 | |
| Stirring | [min] | 55 | 90 | | 90 | 55 | | 55 | 55 | |
| Sample | | A | B | C | A | B | C | A | B | C |
| FII | [IU/ml] | 1.30 | <0.014 | <0.014 | 1.23 | <0.014 | <0.014 | 1.22 | <0.014 | <0.014 |
| FVII | [IU/ml] | 7.3 | <0.015 | <0.015 | 8.6 | <0.015 | <0.015 | 8.3 | <0.015 | <0.015 |
| FVIIa | [mIU/ml] | 4975 | <8.4 | <8.4 | 3645 | <8.4 | <8.4 | 4277 | <8.4 | <8.4 |
| FIX | [IU/ml] | 9.13 | <0.016 | <0.016 | 5.55 | 0.24 | <0.016 | 9.13 | <0.016 | <0.016 |
| FIXa | [mIU/ml] | 327.1 | <1.12 | <1.12 | 355.8 | <1.12 | <1.12 | 329.6 | <1.12 | <1.12 |
| FX | [IU/ml] | 0.38 | <0.015 | <0.015 | 0.25 | <0.015 | <0.015 | 0.38 | <0.015 | <0.015 |
| FXI | [IU/ml] | 6.92 | <0.014 | <0.014 | 4.42 | <0.014 | <0.014 | 6.92 | <0.014 | <0.014 |
| FXIa | [mU/ml] | 296.0 | 1.3 | <0.32 | 128.2 | .83 | <0.32 | 172.5 | 1.4 | <0.32 |
| Organic acid/salt | | caprylic | caprylic | | caprylic | caprylic | | caprylic | caprylic | |
| Organic acid/salt | [mM] | 20 | 10 | | 20 | 10 | | 20 | 10 | |
| pH value | | 4.7 | 4.7 | | 4.7 | 4.7 | | 4.7 | 4.7 | |
| Temperatur | [° C.] | 8 | 27 | | 8 | 21 | | 8 | 21 | |
| Stirring | [min] | 55 | 55 | | 90 | 55 | | 55 | 90 | |
| Sample | | A | B | C | A | B | C | A | B | C |
| FII | [IU/ml] | 0.72 | <0.014 | <0.014 | 0.46 | <0.014 | <0.014 | 0.7 | <0.014 | <0.014 |
| FVII | [IU/ml] | 6.18 | 0.05 | <0.015 | 5.80 | <0.015 | <0.015 | 5.48 | <0.015 | <0.015 |
| FVIIa | [mIU/ml] | 3736 | 23.1 | <8.4 | 3990 | 8.7 | <8.4 | 3821 | <8.4 | <8.4 |
| FIX | [IU/ml] | 5.02 | 0.86 | <0.016 | 4.66 | 0.026 | <0.016 | 6.00 | 0.02 | <0.016 |
| FIXa | [mIU/ml] | 292.6 | 6.59 | <1.12 | 292.4 | 2.86 | <1.12 | 233.2 | 1.76 | <1.12 |
| FX | [IU/ml] | 0.26 | <0.015 | <0.015 | 0.24 | <0.015 | <0.015 | 0.29 | <0.015 | <0.015 |
| FXI | [IU/ml] | 4.85 | 0.096 | <0.014 | 4.89 | 0.035 | <0.014 | 5.32 | 0.03 | <0.014 |
| FXIa | [mU/ml] | 332.4 | 16.6 | <0.32 | 293.1 | 6.8 | <0.32 | 232.2 | 4.6 | <0.32 |
| Organic acid/salt | | caprylic | caprylic | | caprylic | caprylic | | caprylic | caprylic | |
| Organic acid/salt | [mM] | 20 | 10 | | 20 | 10 | | 20 | 10 | |
| pH value | | 4.7 | 4.7 | | 4.7 | 4.7 | | 4.7 | 4.7 | |
| Temperatur | [° C.] | 2 | 27 | | 2 | 27 | | 2 | 21 | |
| Stirring | [min] | 90 | 55 | | 55 | 90 | | 90 | 90 | |
| Sample | | A | B | C | A | B | C | A | B | C |
| FII | [IU/ml] | 0.75 | <0.014 | <0.014 | 0.68 | <0.014 | <0.014 | 0.8 | <0.014 | <0.014 |
| FVII | [IU/ml] | 5.37 | 0.02 | <0.015 | 6.41 | 0.03 | <0.015 | 6.26 | <0.015 | <0.015 |
| FVIIa | [mIU/ml] | 4507 | 11.9 | <8.4 | 4197 | 27 | <8.4 | 4212 | 8.8 | <8.4 |
| FIX | [IU/ml] | 6.72 | 0.051 | <0.016 | 6.20 | 0.099 | <0.016 | 5.66 | 0.029 | <0.016 |
| FIXa | [mIU/ml] | 289.0 | 3.43 | <1.12 | 256.9 | 6.58 | <1.12 | 263.2 | 2.17 | <1.12 |
| FX | [IU/ml] | 0.27 | <0.015 | <0.015 | 0.32 | <0.015 | <0.015 | 0.34 | <0.015 | <0.015 |
| FXI | [IU/ml] | 7.31 | 0.05 | <0.014 | 6.76 | 0.11 | <0.014 | 5.46 | 0.033 | <0.014 |
| FXIa | [mU/ml] | 371.8 | 8.9 | <0.32 | 451.1 | 36.2 | <0.32 | 413.3 | 16 | <0.32 |

TABLE 4-continued

| Precipitations with pH value kept constant | | | | | | | | | | |
|---|---|---|---|---|---|---|---|---|---|---|
| Organic acid/salt | | | caprylic | caprylic | | caprylic | caprylic | | caprylic | caprylic |
| Organic acid/salt | [mM] | | 20 | 10 | | 20 | 20 | | 20 | 10 |
| pH value | | | 4.9 | 4.9 | | 4.9 | 4.9 | | 4.9 | 4.9 |
| Temperatur | [° C.] | | 8 | 24 | | 5 | 27 | | 5 | 24 |
| Stirring | [min] | | 70 | 70 | | 70 | 70 | | 90 | 70 |
| Sample | | | A | B | C | A | B | C | A | B | C |
| FII | [IU/ml] | | 1.32 | <0.014 | <0.014 | 1.2 | <0.014 | <0.014 | 1.51 | <0.014 | <0.014 |
| FVII | [IU/ml] | | 6.77 | <0.015 | <0.015 | 6.37 | 0.02 | <0.015 | 7.09 | 0.02 | <0.015 |
| FVIIa | [mIU/ml] | | 4240 | <8.4 | <8.4 | 4067 | 11 | <8.4 | 5693 | <8.4 | <8.4 |
| FIX | [IU/ml] | | 5.95 | <0.016 | <0.016 | 5.78 | 0.026 | <0.016 | 7.99 | 0.029 | <0.016 |
| FIXa | [mIU/ml] | | 219.4 | 1.75 | <1.12 | 272.1 | 2.05 | <1.12 | 397.1 | 2.12 | <1.12 |
| FX | [IU/ml] | | 0.70 | <0.015 | <0.015 | 0.64 | <0.015 | <0.015 | 0.65 | <0.015 | <0.015 |
| FXI | [IU/ml[ | | 4.72 | 0.017 | <0.014 | 5.02 | 0.032 | <0.014 | 6.95 | 0.033 | <0.014 |
| FXIa | [mU/ml] | | 234 | 5.1 | <0.32 | 243 | 9.7 | <0.32 | 217 | 8.2 | <0.32 |
| | Organic acid/salt | | | | caprylic | caprylic | | caprylic | caprylic | |
| | Organic acid/salt | [mM] | | | 20 | 10 | | 20 | 10 | |
| | pH value | | | | 4.9 | 4.9 | | 4.9 | 4.9 | |
| | Temperatur | [° C.] | | | 5 | 24 | | 5 | 24 | |
| | Stirring | [min] | | | 70 | 90 | | 120 | 70 | |
| | Sample | | | | A | B | C | A | B | C |
| | FII | [IU/ml] | | | 1.20 | <0.014 | <0.014 | 1.10 | <0.014 | <0.014 |
| | FVII | [IU/ml] | | | 5.50 | <0.015 | <0.015 | 5.78 | <0.015 | <0.015 |
| | FVIIa | [mIU/ml] | | | 4093 | <8.4 | <8.4 | 3888 | <8.4 | <8.4 |
| | FIX | [IU/ml] | | | 6.36 | 0.022 | <0.016 | 4.67 | <0.016 | <0.016 |
| | FIXa | [mIU/ml] | | | 365.6 | 2.07 | <1.12 | 281.0 | <1.12 | <1.12 |
| | FX | [IU/ml] | | | 0.49 | <0.015 | <0.015 | 0.48 | <0.015 | <0.015 |
| | FXI | [IU/ml] | | | 5.50 | 0.027 | <0.014 | 2.82 | <0.014 | <0.014 |
| | FXIa | [mU/ml] | | | 144 | 8.0 | <0.32 | 106 | 3.90 | <0.32 |

TABLE 5

| Precipitations with pH values increasing | | | | | | | | | | |
|---|---|---|---|---|---|---|---|---|---|---|
| Organic acid/salt | | | caprylic | caprylic | | caprylic | caprylic | | caprylic | caprylic |
| Organic acid/salt | [mM] | | 20 | 10 | | 20 | 10 | | 20 | 10 |
| pH value | | | 4.7 | 5.1 | | 4.7 | 5.1 | | 4.7 | 5.1 |
| Temperatur | [° C.] | | 8 | 27 | | 8 | 21 | | 2 | 27 |
| Stirring | [min] | | 90 | 90 | | 55 | 55 | | 15 | 55 |
| Sample | | | A | B | C | A | B | C | A | B | C |
| FII | [IU/ml] | | 0.51 | 0.015 | <0.014 | 0.4 | <0.014 | <0.014 | 0.58 | <0.014 | <0.014 |
| FVII | [IU/ml] | | 4.55 | 0.019 | <0.015 | 4.40 | <0.015 | <0.015 | 5.70 | 0.018 | <0.015 |
| FVIIa | [mIU/ml] | | 3945 | 27 | <8.4 | 3384 | <8.4 | <8.4 | 3625 | 9.9 | <8.4 |
| FIX | [IU/ml] | | 3.38 | 0.08 | <0.016 | 3.90 | 0.06 | <0.016 | 4.60 | 0.08 | <0.016 |
| FIXa | [mIU/ml] | | 269.3 | 12 | <1.12 | 215.7 | 3.04 | <1.12 | 273.0 | 4.62 | <1.12 |
| FX | [IU/ml] | | 0.19 | <0.015 | <0.015 | 0.20 | <0.015 | <0.015 | 0.19 | <0.015 | <0.015 |
| FXI | [IU/ml] | | 3.38 | 0.08 | <0.014 | 4.91 | 0.10 | <0.014 | 6.16 | 0.13 | <0.014 |
| FXIa | [mU/ml] | | 524 | 39.0 | <0.32 | 362 | 18.90 | <0.32 | 336 | 13.5 | <0.32 |
| Organic acid/salt | | | caprylic | caprylic | | caprylic | caprylic | | caprylic | caprylic |
| Organic acid/salt | [mM] | | 20 | 10 | | 20 | 10 | | 20 | 10 |
| pH value | | | 4.7 | 5.1 | | 4.7 | 5.1 | | 4.9 | 5.1 |
| Temperatur | [° C.] | | 2 | 21 | | 2 | 21 | | 5 | 24 |
| Stirring | [min] | | 90 | 55 | | 55 | 90 | | 70 | 70 |
| Sample | | | A | B | C | A | B | C | A | B | C |
| FII | [IU/ml] | | 0.56 | <0.014 | <0.014 | 0.5 | <0.014 | <0.014 | 1.20 | <0.014 | <0.014 |
| FVII | [IU/ml] | | 5.30 | 0.027 | <0.015 | 4.20 | <0.015 | <0.015 | 6.23 | 0.02 | <0.015 |
| FVIIa | [mIU/ml] | | 3529 | 19.2 | <8.4 | 3374 | 10.2 | <8.4 | 7395 | 13.4 | <8.4 |
| FIX | [IU/ml] | | 4.90 | 0.16 | <0.016 | 4.40 | 0.08 | <0.016 | 8.62 | 0.046 | <0.016 |
| FIXa | [mIU/ml] | | 270.6 | 7.85 | <1.12 | 261.1 | 4.8 | <1.12 | 320.0 | 2.11 | <1.12 |

TABLE 5-continued

| | | \multicolumn{9}{c}{Precipitations with pH values increasing} |
|---|---|---|---|---|---|---|---|---|---|---|

| | | | | | | | | | | |
|---|---|---|---|---|---|---|---|---|---|
| FX | [IU/ml] | 0.30 | <0.015 | <0.015 | 0.20 | <0.015 | <0.015 | 0.32 | <0.015 | <0.015 |
| FXI | [IU/ml] | 6.71 | 0.23 | <0.014 | 5.70 | 0.11 | <0.014 | 7.63 | 0.039 | <0.014 |
| FXIa | [mU/ml] | 346 | 26.8 | <0.32 | 291 | 18.1 | <0.32 | 266.2 | 8.8 | <0.32 |

TABLE 6

Precipitations with pH values decreasing

| Organic acid/salt | | caprylic | caprylic | | caprylic | caprylic | | caprylic | caprylic |
|---|---|---|---|---|---|---|---|---|---|
| Organic acid/salt | [mM] | 20 | 10 | | 20 | 10 | | 20 | 10 |
| pH value | | 5.1 | 4.7 | | 5.1 | 4.9 | | 5.1 | 4.7 |
| Temperatur | [° C.] | 8 | 27 | | 5 | 24 | | 2 | 27 |
| Stirring | [min] | 90 | 90 | | 70 | 70 | | 55 | 55 |
| Sample | | A | B | C | A | B | C | A | B | C |
| FII | [IU/ml] | 1.20 | 0.014 | <0.014 | 1.28 | <0.014 | <0.014 | 0.87 | <0.014 | <0.014 |
| FVII | [IU/ml] | 4.92 | <0.015 | <0.015 | 7.49 | <0.015 | <0.015 | 8.2 | <0.015 | <0.015 |
| FVIIa | [mIU/ml] | 4240 | <8.4 | <8.4 | 5040 | <8.4 | <8.4 | 4667 | <8.4 | <8.4 |
| FIX | [IU/ml] | 5.84 | <0.016 | <0.016 | 11.47 | <0.016 | <0.016 | 7.11 | <0.016 | <0.016 |
| FIXa | [mIU/ml] | 317.7 | <1.12 | <1.12 | 340.3 | <1.12 | <1.12 | 304.8 | <1.12 | <1.12 |
| FX | [IU/ml] | 0.21 | <0.015 | <0.015 | 0.32 | <0.015 | <0.015 | 0.17 | <0.015 | <0.015 |
| FXI | [IU/ml] | 4.72 | <0.014 | <0.014 | 7.97 | <0.014 | <0.014 | 5.25 | <0.014 | <0.014 |
| FXIa | [mU/ml] | 221 | 0.45 | <0.32 | 175.1 | 2.2 | <0.32 | 183.0 | 1.0 | <0.32 |

| Organic acid/salt | | caprylic | caprylic | | caprylic | caprylic |
|---|---|---|---|---|---|---|
| Organic acid/salt | [mM] | 20 | 10 | | 20 | 10 |
| pH value | | 5.1 | 4.7 | | 5.1 | 4.7 |
| Temperatur | [° C.] | 2 | 21 | | 2 | 21 |
| Stirring | [min] | 90 | 55 | | 55 | 90 |
| Sample | | A | B | C | A | B | C |
| FII | [IU/ml] | 0.98 | <0.014 | <0.014 | 0.92 | <0.014 | <0.014 |
| FVII | [IU/ml] | 7.20 | <0.015 | <0.015 | 7.00 | <0.015 | <0.015 |
| FVIIa | [mIU/ml] | 4263 | <8.4 | <8.4 | 4195 | <8.4 | <8.4 |
| FIX | [IU/ml] | 8.98 | <0.016 | <0.016 | 7.86 | <0.016 | <0.016 |
| FIXa | [mIU/ml] | 294.8 | <1.12 | <1.12 | 314.3 | <1.12 | <1.12 |
| FX | [IU/ml] | 0.13 | <0.015 | <0.015 | 0.18 | <0.015 | <0.015 |
| FXI | [IU/ml] | 2.46 | <0.014 | <0.014 | 6.78 | <0.014 | <0.014 |
| FXIa | [mU/ml] | 189.0 | 0.7 | <0.32 | 153.0 | 0.6 | <0.32 |

TABLE 7

Precipitations with capric acid/salt

| Organic acid/salt | | capric | capric | | capric | capric | |
|---|---|---|---|---|---|---|---|
| Organic acid/salt | [mM] | 20 | 10 | | 20 | 10 | |
| pH value | | 4.9 | 4.9 | | 5.2 | 5.2 | |
| Temperatur | [° C.] | 5 | 25 | | 5 | 25 | |
| Stirring | [min] | 60 | 60 | | 60 | 60 | |
| Sample | | A | B | C | A | B | C |
| FII | [IU/ml] | na | na | na | 0.4 | <0.014 | <0.014 |
| FVII | [IU/ml] | 15.5 | 1.7 | <0.015 | 4.3 | 0.32 | <0.015 |
| FVIIa | [mIU/ml] | 3945 | 1228 | <8.4 | 2805 | 173 | <8.4 |
| FIX | [IU/ml] | 8.3 | na | <0.016 | 3.2 | 0.084 | <0.016 |
| FIXa | [mIU/ml] | 368 | 90 | <1.12 | 150 | 7.31 | <1.12 |
| FX | [IU/ml] | 0.22 | 0.015 | <0.015 | 0.05 | <0.015 | <0.015 |
| FXI | [IU/ml] | na | 0.41 | <0.014 | 1.95 | <0.014 | <0.014 |
| FXIa | [mU/ml] | 102 | 22.4 | <1.0 | 107.9 | 3 | <1.0 |

TABLE 8

Precipitations with caprylic acid performed with the same starting material; influence of pH values and concentrations

| Organic acid/salt | | caprylic | caprylic | caprylic | caprylic | caprylic | caprylic | caprylic | caprylic | caprylic |
|---|---|---|---|---|---|---|---|---|---|---|
| Organic acid/salt | [mM] | 10 | 30 | 40 | 10 | 30 | 40 | 10 | 30 | 40 |
| pH value | | 5.5 | 5.5 | 5.5 | 5.0 | 5.0 | 5.0 | 4.7 | 4.7 | 4.7 |
| Sample | | B | B | B | B | B | B | B | B | B |
| FII | [IU/ml] | <0.014 | <0.014 | <0.014 | <0.014 | <0.014 | <0.014 | 0.024 | <0.014 | <0.014 |
| FVII | [IU/ml] | 0.073 | <0.015 | <0.015 | 0.062 | <0.015 | <0.015 | 0.13 | <0.015 | <0.015 |
| FVIIa | [mIU/ml] | 21 | <8.4 | <8.4 | 26 | <8.4 | <8.4 | 90 | 13 | <8.4 |
| FIX | [IU/ml] | <0.016 | <0.016 | <0.016 | 0.066 | <0.016 | <0.016 | 0.249 | 0.04 | <0.016 |
| FIXa | [mIU/ml] | <1.12 | <1.12 | <1.12 | 2.68 | <1.12 | <1.12 | 18.75 | 5.09 | <1.12 |
| FX | [IU/ml] | <0.015 | <0.015 | <0.015 | <0.015 | <0.015 | <0.015 | 0.022 | <0.015 | <0.015 |
| FXI | [IU/ml] | <0.014 | <0.014 | <0.014 | 0.055 | <0.014 | <0.014 | 0.448 | 0.072 | <0.014 |
| FXIa | [mU/ml] | 2.8 | 2.0 | 1.8 | 6.1 | 1.3 | 1.3 | 44.9 | 30.5 | 2.4 |

The invention claimed is:

1. A method for purifying a protein containing solution, obtained from blood, blood plasma, a plasma function, or by recombinant methods, comprising the step of
contacting the protein containing solution, while stirring, with an organic acid or its salt, wherein the organic acid is selected from the group consisting of valeric acid (C5), capric acid (C10), and a combination thereof, to inactivate and remove from the solution coagulation factors selected from the group consisting of FII, FVII, FVIIa, FIX, FIXa, FX, FXI, and FXIa to obtain a purified protein containing solution.

2. The method of claim 1 wherein the method comprises contacting of the solution with the organic acid or its salt at a temperature of about 1 to about 40° C.

3. The method of claim 1 wherein the method comprises a first contacting of the solution with the organic acid or its salt at a temperature of about 2 to about 8° C. and a second contacting with the same acid or its salt or a different acid or its salt at a temperature of about 20 to about 30° C.

4. The method of claim 1 wherein the contacting takes place within a pH range of from 4.0 to 6.0.

5. The method of claim 1 wherein the contacting takes place within a pH range of from 4.2 to 5.6.

6. The method of claim 1 wherein the organic acid or its salt is added to the protein containing solution to a concentration of from 5 to 50 mmol/l.

7. The method of claim 1 wherein the organic acid or its salts is added to the protein containing solution to a concentration of from 10 to 22 mmol/l.

8. The method of claim 1 wherein the organic acid or its salt containing protein solution is stirred for 45 to 180 minutes.

9. The method of claim 1 wherein the organic acid or its salt containing protein solution is stirred for 55 to 120 minutes.

10. The method of claim 1 wherein the organic acid or its salt containing protein solution is stirred in the presence of naturally occurring or synthesized silicates.

11. The method of claim 1 wherein a supernatant is produced from the organic acid or its salt containing protein solution after stirring by separation methods selected from filtration, settlement or centrifugation.

12. The method of claim 1 wherein the method also comprises anion exchange chromatography, solvent/detergent treatment, nanofiltration, ultrafiltration, diafiltration, formulation, sterile filtration, filling into final containers and optionally lyophilization.

* * * * *